US010986998B2

(12) United States Patent
Tichauer et al.

(10) Patent No.: US 10,986,998 B2
(45) Date of Patent: Apr. 27, 2021

(54) APPARATUS AND METHOD FOR ENHANCED EARLY PHOTON DETECTION IN OPTICAL PROJECTION TOMOGRAPHY

(71) Applicants: Kenneth M. Tichauer, Chicago, IL (US); Jovan G. Brankov, Evanston, IL (US); Lagnojita Sinha, Chicago, IL (US)

(72) Inventors: Kenneth M. Tichauer, Chicago, IL (US); Jovan G. Brankov, Evanston, IL (US); Lagnojita Sinha, Chicago, IL (US)

(73) Assignee: ILLINOIS INSTITUTE OF TECHNOLOGY, Chicago, IL (US)

( * ) Notice: Subject to any disclaimer, the term of this patent is extended or adjusted under 35 U.S.C. 154(b) by 571 days.

(21) Appl. No.: 15/497,407

(22) Filed: Apr. 26, 2017

(65) Prior Publication Data

US 2017/0303789 A1 Oct. 26, 2017

Related U.S. Application Data

(60) Provisional application No. 62/327,800, filed on Apr. 26, 2016.

(51) Int. Cl.
*A61B 5/00* (2006.01)
*G01N 21/64* (2006.01)
*H01L 31/107* (2006.01)

(52) U.S. Cl.
CPC .......... *A61B 5/0073* (2013.01); *A61B 5/0071* (2013.01); *G01N 21/64* (2013.01);
(Continued)

(58) Field of Classification Search
CPC ................ A61B 5/0073; A61B 5/0071; A61B 2562/0233; A61B 2576/00; G01N 21/64;
(Continued)

(56) References Cited

U.S. PATENT DOCUMENTS

| 8,314,406 B2 | 11/2012 | Ntziachristos et al. |
| 2004/0089817 A1 | 5/2004 | Long et al. |

(Continued)

FOREIGN PATENT DOCUMENTS

| WO | WO-2014127145 A1 * | 8/2014 | ........... A61B 5/0071 |
| WO | WO 2014/173644 A1 | 10/2014 | |

OTHER PUBLICATIONS

Yang, Y., Shi, J., Cao, F., Peng, J., & Zeng, G. (2015). Computational imaging based on time-correlated single-photon-counting technique at low light level. Applied optics, 54(31), 9277-9283. (Year: 2015).*

(Continued)

*Primary Examiner* — Michael J Tsai
*Assistant Examiner* — Johnathan Maynard
(74) *Attorney, Agent, or Firm* — Pauley Erickson & Swanson (57) ABSTRACT

A system and method for optical tomography including illuminating an object with pulsing stimulus light and pulsing the stimulus light at a repetition frequency having a pulse period that is greater than a dead-time of a detector. Coordinating the pulse with the dead-time of the detector allows for higher powered light source and improves early photon detection.

11 Claims, 7 Drawing Sheets

(52) U.S. Cl.
CPC .... *H01L 31/107* (2013.01); *A61B 2562/0233* (2013.01); *A61B 2576/00* (2013.01); *G01N 21/6456* (2013.01); *G01N 2201/0697* (2013.01); *G01N 2201/06113* (2013.01); *G01N 2201/12* (2013.01)

(58) Field of Classification Search
CPC ..... G01N 21/6456; G01N 2201/06113; G01N 2201/0697; G01N 2201/12; H01L 31/107
See application file for complete search history.

(56) References Cited

U.S. PATENT DOCUMENTS

| | | |
|---|---|---|
| 2014/0078491 A1 | 3/2014 | Eisele et al. |
| 2015/0063527 A1 | 3/2015 | Daerr et al. |
| 2015/0066436 A1 | 3/2015 | Elliott et al. |
| 2015/0374308 A1* | 12/2015 | Tichauer ............ A61B 5/7278 600/431 |

OTHER PUBLICATIONS

Thomas, A., Bowsher, J., Roper, J., Oliver, T., Dewhirst, M., & Oldham, M. (2010). A comprehensive method for optical-emission computed tomography. Physics in Medicine & Biology, 55(14), 3947. (Year: 2010).*
Yang, Y., Shi, J., Cao, F., Peng, J., & Zeng, G. (2015). Computational imaging based on time-correlated single-photon-counting technique at low light level. Applied optics, 54(31), 9277-9283. (Year: 2015).*
Wang, L., Ho, P. P., Liu, C., Zhang, G., & Alfano, R. R. (1991). Ballistic 2-D imaging through scattering walls using an ultrafast optical Kerr gate. Science, 253(5021), 769-771. (Year: 1991).*
Tan, W., Zhou, Z., Lin, A., Si, J., Zhan, P., Wu, B., & Hou, X. (2013). High contrast ballistic imaging using femtosecond optical Kerr gate of tellurite glass. Optics express, 21(6), 7740-7747. (Year: 2013).*
Bassi, A., Brida, D., D'Andrea, C., Valentini, G., Cubeddu, R., De Silvestri, S., & Cerullo, G. (2010). Time-gated optical projection tomography. Optics letters, 35(16), 2732-2734. (Year: 2013).*
Thomas, A., Bowsher, J., Roper, J., Oliver, T., Dewhirst, M., & Oldham, M. (2010). A comprehensive method for optical-emission computed tomography. Physics in Medicine & Biology, 55(14), 3947. (Year: 2010).*
Peronio, P., Acconcia, G., Rech, I., & Ghioni, M. (2015). Improving the counting efficiency in time-correlated single photon counting experiments by dead-time optimization. Review of Scientific Instruments, 86(11), 113101. (Year: 2015).*
Mu, Y., Valim, N., & Niedre, M. (2013). Evaluation of a fast single-photon avalanche photodiode for measurement of early transmitted photons through diffusive media. Optics letters, 38(12), 2098-2100. (Year: 2013).*
Mu, Y., & Niedre, M. (2015). Fast single photon avalanche photodiode-based time-resolved diffuse optical tomography scanner. Biomedical optics express, 6(9), 3596-3609. (Year: 2015).*
Tyndall, D., Rae, B. R., Li, D. D. U., Arlt, J., Johnston, A., Richardson, J. A., & Henderson, R. K. (2012). A High-Throughput Time-Resolved Mini-Silicon Photomultiplier With Embedded Fluorescence Lifetime Estimation in 0.13 mum CMOS. IEEE Transactions on Biomedical Circuits and Systems, 6(6), 562-570 (Year: 2012).*
Niedre, M. J., de Kleine, R. H., Aikawa, E., Kirsch, D. G., Weissleder, R., & Ntziachristos, V. (2008). Early photon tomography allows fluorescence detection of lung carcinomas and disease progression in mice in vivo. Proceedings of the National Academy of Sciences, 105(49), 19126-19131. (Year: 2008).*
PCT International Search Report, Form PCT/ISA/210, dated Sep. 1, 2017, (4 pages).
PCT Written Opinion of the International Searching Authority, Form PCT/ISA/237, dated Sep. 1, 2017, (5 pages).
Charbon, E., et al., "SPAD-Based Sensors," TOF Range-Imaging Cameras, Apr. 9, 2013, (28 pages).
Dixon, A.R., et al., "Ultrashort dead time of photon-counting InGaAs avalanche photodiodes," 03.67.Dd Quantum Cryptography, Jun. 9, 2009, (10 pages).
O'Toole, Matthew, et al., "Reconstructing Transient Images from Single-Photon Sensors," May 17, 2017, (9 pages).
EPO, Form EPO Form 1503 03.82, Extended EP Search Report for European Patent Application EP 17 79 0353, dated Nov. 16, 2019 (4 pp.) together with EPO Form 1703 01.91TRI (5 pp.).
Arlt et al.,"A study of pile-up in integrated time-correlated single photon counting systems," Review of Scientific Instruments, vol. 84, No. 10, Jan. 1, 2013, 11 pages.
Pavia et al.,"A 1×400 Backside-Illuminated SPAD Sensor With 49.7 ps Resolution, 30 pJ/Sample TDCs Fabricated in 3D CMOS Technology for Near-Infrared Optical Tomography," IEEE Journal of Solid-State Circuits, IEEE Service Center, vol. 50, No. 10, Oct. 1, 2015, pp. 2406-2418.
Peronio et al.,"Improving the counting efficiency in time-correlated single photon counting experiments by dead-time optimization," Review of Scientific Instruments, vol. 86, No. 11, Nov. 3, 2015, 8 pages.

* cited by examiner

| | Laser power (approx) | Photon count rate at detector | Photon count rate detected |
|---|---|---|---|
| ——— | 0.008 mW | 0.025e7 | 0.025e7 |
| ——— | 50 x 0.008 mW | 1.275e7 | 0.462e7 |
| - - - - | 100 x 0.008 mW | 2.525e7 | 0.497e7 |
| - - - - | 150 x 0.008 mW | 3.775e7 | 0.499e7 |

APPARATUS AND METHOD FOR ENHANCED EARLY PHOTON DETECTION IN OPTICAL PROJECTION TOMOGRAPHY

CROSS REFERENCE TO RELATED APPLICATION

This application claims the benefit of U.S. Provisional Patent Application Ser. No. 62/327,800, filed on 26 Apr. 2016. The Provisional Application is hereby incorporated by reference herein in its entirety and is made a part hereof, including but not limited to those portions which specifically appear hereinafter.

BACKGROUND OF THE INVENTION

This invention relates generally to medical imaging using optical projection tomography and, more particularly, to a method and apparatus capable of achieving high-resolution, quantitative mapping of fluorescence targeted biological molecular concentration distributions, such as in 1-10 mm diameter tissues.

Absorption and fluorescence-based optical tomography has been heralded as a low-cost, ionizing radiation-free alternative to conventional medical imaging modalities for decades, particularly for tissue specimen and small animal imaging. However, a major limitation to optical tomography is the highly scattering nature of photon propagation in biological tissue. This scattering obfuscates the ability to predict the exact path of a detected photon, effectively setting spatial resolution limits of greater than 1 mm, even with the most sophisticated reconstruction approaches. One solution to improving spatial resolution is so-called early-photon tomography. Early photon tomography requires pulsed light sources and advanced time-resolved detection of the transmitted photons so that the earliest arriving photons, having taken the most direct path between source and detector, can be selectively isolated to improve reconstructed image spatial resolution. There is a continuing need for improvements to fluorescence tomography for biological samples.

SUMMARY OF THE INVENTION

The invention improves existing "early photon" optical projection tomography (both absorption and fluorescence based), through use of innovative "pile-up" or "dead-time" effect amplification of early photons to enhance spatial resolution to measure biological molecule concentrations quantitatively.

The general object of the invention can be attained, at least in part, through a method for optical tomography that includes illuminating an object with pulsing stimulus light, and detecting a first excitation or emission photon that arrives at a detector for a pulse of the stimulus light. Additional photons from the pulse arrive at the detector during a dead-time of the detector.

The invention further includes a method for optical tomography that includes illuminating an object with pulsing stimulus light and, pulsing the stimulus light at a repetition frequency having a pulse period that is greater than a dead-time of a detector. This embodiment of the invention allows for detecting the first excitation or emission photon that arrives at the detector for a pulse of the stimulus light, wherein additional photons from the pulse arrive at the detector during the dead-time of the detector.

The invention further includes a system or device to implement the methods. In embodiments of this invention, a system or device for generating fluorescence data of fluorophores in tissue of a subject includes a pulsing stimulation apparatus that generates a pulsing light of a stimulus wavelength to illuminate the tissue. A photodetector is included to capture data of first excitation or emission photon wavelengths for the pulses of the pulsing light. The pulsing stimulation apparatus has a repetition frequency with a pulse period that is greater than a dead-time of the photodetector to capture early photons. A suitable computer or data processor, along with a non-transitory recordable medium configured to store the data is provided to control the components and record and/or analyze the data.

The method and apparatus of the invention significantly enhances detection of early-arriving photons. The invention provides for detection of orders-of-magnitude more rare, early photons, whereas later photons arrive during a dead-time of the detector. By coordinating the light pulse with the dead-time, later arriving photons for a pulse are not recorded and/or captured by the detector after the dead-time ends and the detector is detecting again, thereby providing higher rates of early photon capture.

The invention allows for and desirably uses higher power light sources, resulting in greater photon capture per pulse amount than existing systems. Embodiments of this invention leverage the robustness of, for example, single photon avalanche photodiode (SPAD) detectors, which in turn allows for high power illumination. This level of illumination would normally be avoided because of saturation effects, however, if a pulsed-laser (pulsed at a period longer than the dead-time of the detector) is used to illuminate the detector, the pulse is correlated with the dead-time, and/or detected photon events are time-stamped through time-correlated single photon counting, it is possible to ensure the saturation only effects "later-arriving" photons and allows for much higher count rates of early-arriving photons. Since early photons typically take a path of shorter distance between source and detector than later-arriving photons when transilluminating a light scattering object (like biological tissue), it is possible to significantly improve optical tomography using this innovative approach.

Embodiments of this invention can be applied or combined with the benefits of dual-wavelength early photon techniques to enable paired-agent molecular imaging, which is a powerful approach for extracting quantitative molecular information in biological samples. Together, the enhanced early photon detection and the paired-agent imaging characteristics of the system can provide a map of biological molecule concentrations in three-dimensional tissues with a sensitivity and spatial resolution that is orders-of-magnitude better than any existing comparable system.

As used herein, references to "dead-time" are to be understood to refer to a time in which a detector is inactive or unable to detect, and more particularly, to the period after the recording of a particle or pulse photon when a detector is unable to record another particle or pulse photon.

Other objects and advantages will be apparent to those skilled in the art from the following detailed description taken in conjunction with the appended claims and drawings.

DESCRIPTION OF THE INVENTION

The invention provides a method and apparatus or system for "early photon" optical projection tomography. The invention combines and correlates an excitation light pulse rate with a detector dead-time to enhance spatial resolution. The invention is beneficially transformative in, for example, at least three areas: 1) cancer researchers can use it to explore connections between drug resistance and molecular heterogeneity; 2) drug developers can use it to quantitatively map, drug delivery, and more importantly, drug binding (not possible with existing in vivo technologies) in 3D—these could allow increased investment in the drugs with the greatest benefits for patients; and 3) the imaging system also has a clinical potential as a means of improving cancer staging by enhancing sensitivity of lymph node pathology.

The invention includes a method for optical tomography that begins with illuminating an object, such as a tissue of a patient, with a pulsing stimulus light. A detector is paired with the pulsing light to capture an excitation or emission photon from the object that results from the pulsing light impacting the object. Many, if not most or all, of the light pulses according to this invention result in a plurality of photons emitting from the object. The method of this invention correlates the timing of the pulse with a predetermined dead-time of the detector to ensure that after a first, early photon particle is detected, the remaining photons from the pulse arrive at the detector during the detector dead-time.

The detector then 'reactivates' ready to capture the first photon from a subsequent pulse. In embodiments of this invention, stimulus light is pulsed at a pulse period that is greater than a dead-time of the detector. The pulsing of the stimulus light is desirably at a repetition frequency that is less than the inverse of a dead-time of the detector.

The method and apparatus of this invention allow for use of increased stimulus light power over current methods, and relative to the object to be imaged. Current commercial systems use light-sources, e.g., lasers, powered to result in a photon capture rate of less than 5% (i.e., 5 photons are captured for every 100 pulses). Using conventional fluorescent imaging, photon capture rates above 5% result in resolution issues, due at least in part to the detectors and photon scattering. Some currently available systems even provide warnings if the capture rate approaches 5%. Unlike conventional systems, this invention uses light source powers that provide a detector photon capture rate of greater than 5%, greater than 6%, desirably at least 20%, more desirably greater than 50%, even more desirably greater than 75%, and preferably higher than 90%. The light source power of this invention selected can be relative to the tissue type and size, but since the pulse/dead-time correlation provides a detection count rate that exceeds a pile-up effect limit, the higher power light source and suitable detectors can be used without the negative effects of current systems.

Figure 1:
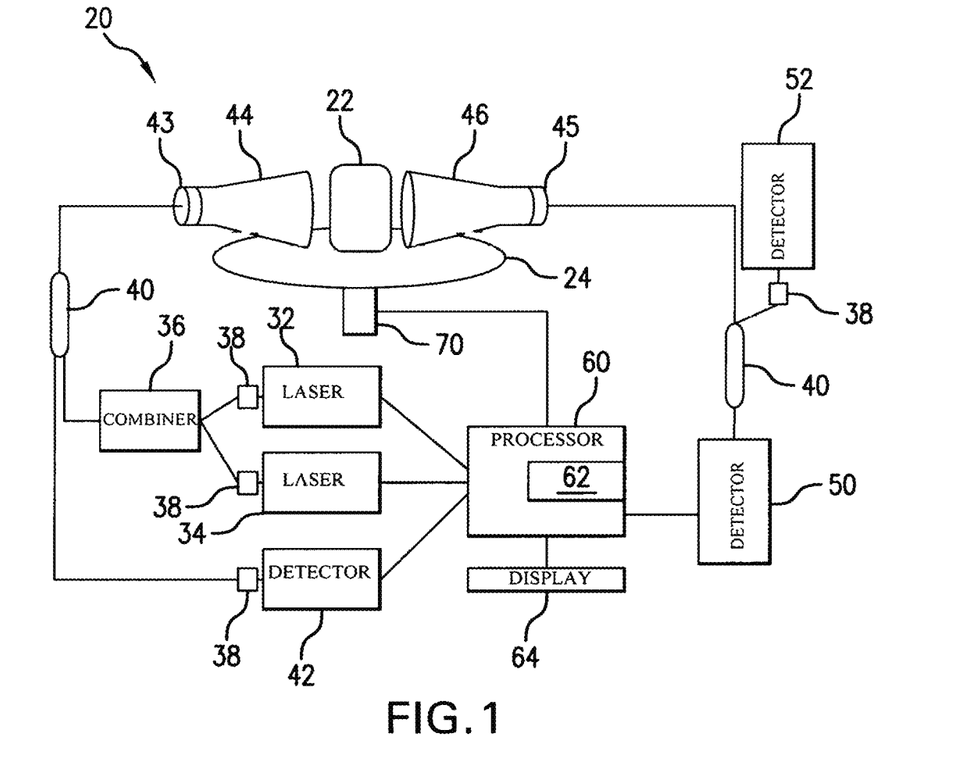
FIG. 1 is a block diagram of a fluorescent imaging system according to one embodiment of this invention.

FIG. 1 illustratively shows an apparatus or system 20 for generating fluorescence data of fluorophores in an object or subject according to one embodiment of this invention. In FIG. 1, the object to be imaged, such as tissue sample 22, is placed between a pulsing stimulation apparatus 30 and a detector 50. The tissue 22 can be placed on a rotating or otherwise moveable stage 24 for improved imaging.

The pulsing stimulation apparatus 30 in FIG. 1 includes at least one laser 32, and is shown with two lasers 32 and 34. Two lasers, such as providing two different wavelengths (e.g. 685 and 785 nm lasers) optionally allow for the invention to be used with the dual-light source method of Tichauer et al., U.S. Patent Application Publication 2015/0374308, herein incorporated by reference. The two lasers 32 and 34 are fiber-coupled and combined, such as via a mechanized variable attenuator (VA) 38, in an in-line fiber combiner 36. The combined pulses are then sent to a beamsplitter 40 and a portion, such as about 4%, of the light is sent to a time-correlated single photon counting (TCSPC) detector 42 to monitor the laser pulses. The remaining, e.g., 96%, of the light is sent through a collimator 43 to a telecentric scanning lens 44 to scan over the surface of the tissue specimen 22. A corresponding telecentric scanning lens 46, in combination with a fiber coupling lens 45, is positioned opposite the excitation spot to collect light in a parallel geometry. That light is then split between two time-gated TCSPC detectors: e.g., 96% of the light sent to the fluorescence detector 50, and 4% sent to the transmittance detector 52. As described above, the pulsing stimulation apparatus 30 pulses with a repetition frequency having a pulse period that is greater than a dead-time of the photodetectors 50 and 52. Suitable detectors include single photon counting photodetector, such as single photon avalanche photodiode detectors, or any detector with single photon counting capabilities and desirably a non-extendable dead-time, including all "gated" setups (SHG crystals, gated detectors, etc.). A multichannel photodetector can also be used to capture data with the tissue 22 illuminated at each of a plurality of discrete points in succession.

At least one data processor 60 is in controlling combination with the components, including the pulsing stimulation apparatus 30 and the detectors 50, 52. The data processor 60 includes a non-transitory recordable medium 62 configured to store the data obtained by the detectors 50, 52. The data processor 60 also automatically coordinates the pulsing light of a stimulus wavelength as a function of the dead-time of the photodetector according to the method described herein. For example, the data processor 60 automatically coordinates the pulsing light of a stimulus wavelength at a repetition frequency that is less than the inverse of a dead time of the detector 50. The data collected by the data processor 60 is or is used to form a digital image, which can optionally be displayed on a display 64 in combination with the data processor 60. The data processor further includes machine readable code including instructions for controlling the pulse and detectors and for reconstructing an image and/or three dimensional model of a fluorophore distribution in the tissue from the data.

Various and alternative light sources, detectors, and other elements and configurations are available for the system of this invention. For example, the system can include an administration apparatus 70 to administer a fluorophore contrast agent to the tissue 22.

EXAMPLES

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

Figure 2A:
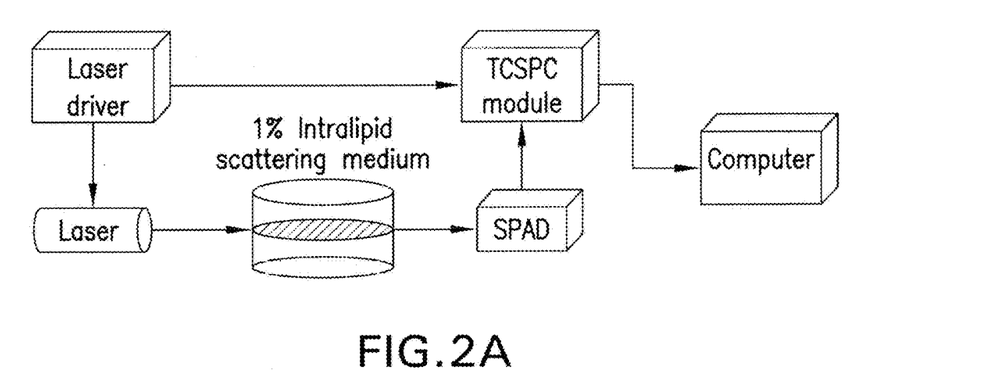
FIG. 2A is a block diagram of a fluorescent imaging system according to one embodiment of this invention.
Figure 2B:
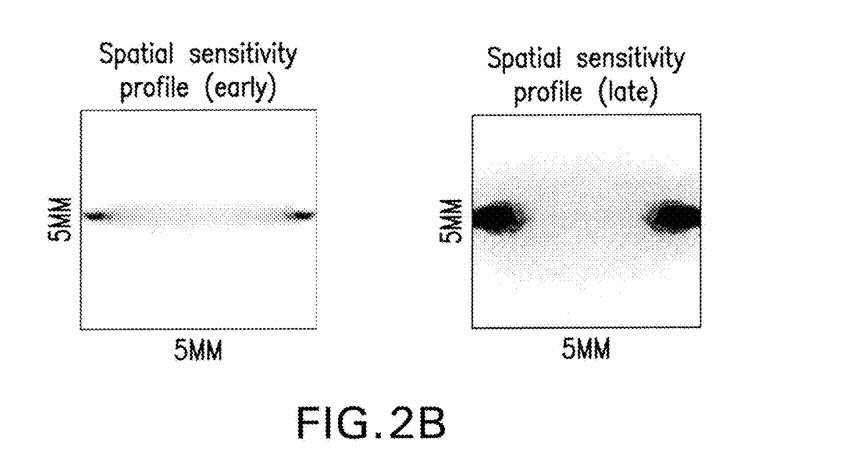
FIG. 2B shows spatial sensitivity profiles obtained with the system of FIG. 2A.

FIG. 2A illustrates an experimental setup of an apparatus according to one embodiment of this invention. FIG. 2B shows the simulated spatial sensitivity profile as observed with only early arriving photons or the ballistic and quasi ballistic photons vs. the late arriving ones which are diffused in the medium and have suffered scattering losses. The experimental setup was built around a single excitation laser at 785 nm (LDH-PC780 and PDL 800-B laser driver, Picoquant, USA) and one state-of-the-art time-correlated single photon counting (TCSPC) (Picoharp 300, Picoquant, USA) single photon avalanche diode (SPAD) (MPD, Picoquant, USA) solid-state detector. The laser was driven by the laser driver, which was synced with the TCSPC module. The SPAD detected the signal coming through the sample (5 mm thick cuvette with 1% intralipid solution) and signaled the TCSPC module for time stamping which was then analyzed by the computer. A mechanized 3-degree-of-freedom translational and rotational stage that was computer controlled was used. All software was developed in MATLAB (Mathworks, Natick, Mass.).

Figure 3A:
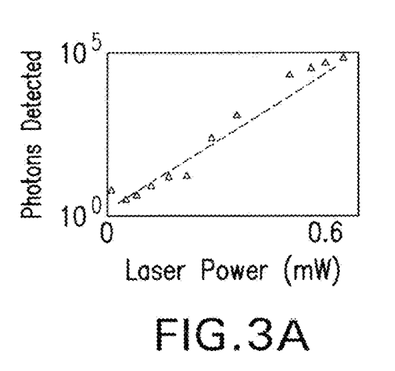
FIG. 3A is a plot showing five orders of linearity of early photons (Δ).
Figure 3B:
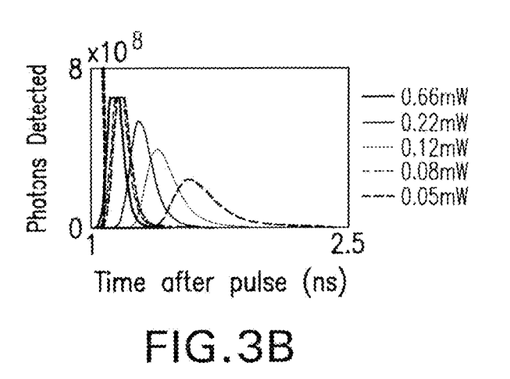
FIG. 3B is a plot showing pile-up effect and drastic improvement in early photon detection according to this invention.
Figure 3C:
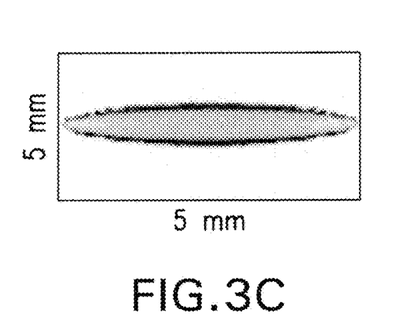
FIG. 3C is a log-scale sensitivity profile of an early photons according to this invention in a 5 mm medium.
Figure 3D:
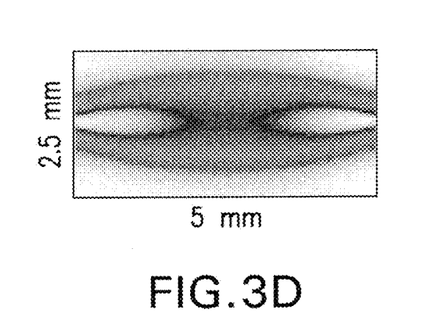
FIG. 3D is a log-scale sensitivity profile for (0-100 ps) photons.
Figure 3E:
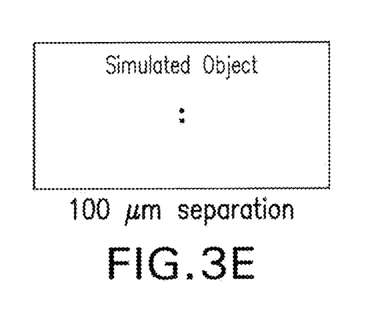
FIG. 3E is a simulation of two 100-μm fluorescent inclusions separated by 100 μm.
Figure 3F:
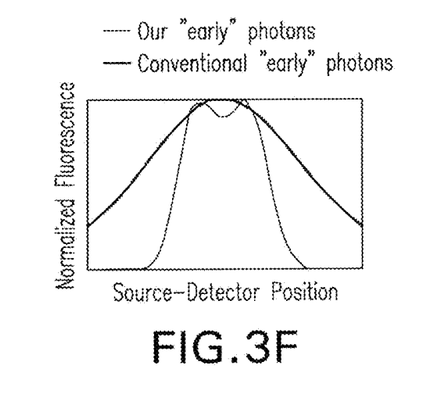
FIG. 3F is a vertical scan profile of early photons and conventional early photons through the object in FIG. 3E.

By leveraging the robustness of the new single photon avalanche photodiode light detectors and the saturation/"pile-up" effect, it was demonstrated that it is possible to significantly increase the number of early photons detected. In conventional TCSPC, count rate is limited by the dead-time of the detector, the pulse rate of the light source (only 1 photon per laser pulse—"pile-up" effect), and how robust the detector is. In the system of FIG. 2, SPAD detectors were used because they are robust to high levels of light, so essentially cannot be damaged by high photon counts. The laser was driven at a detection count rate that far exceeded the pile-up effect limit so that many photons arrive at the detector within a single laser pulse period. Only one of these photons can be detected and it will always be the first photon that arrives. The results show a significant improvement of the count rate of rare early photons, in 7 mm thick scattering medium, at the expense of not needed later arriving photons. Note that without pile-up and saturation effect all curves should be scaled versions of the lowest intensity curve. The number of early photons, photons arriving before the vertical line in FIG. 3B, was linear with laser power even at very high powers.

FIG. 3 summarizes experimental data, and illustrates advantages of using the pile-up effect for early photons according to the apparatus of FIG. 2A. Plot A of FIG. 3 shows five orders of linearity of the early photons (Δ). Plot B of FIG. 3 shows the pile-up effect and drastic improvement in early photon detection (early photon cut-off, dashed line) that can be achieved according to this invention. Profile C of FIG. 3 shows the log-scale sensitivity profile of the early photons according to this invention in a 5 mm medium. Profile D of FIG. 3 shows the log-scale sensitivity profile for (0-100 ps) photons (best possible without pile-up). E of FIG. 3 is a simulation of two 100-μm fluorescent inclusions separated by 100 μm. Plot F of FIG. 3 includes vertical scan profiles of the early photons and conventional early photons through object in E of FIG. 3.

A second example used a method to significantly enhance the detection rate of the earliest possible photons by running laser power high enough to ensure that time-correlated single photon counting (TCSPC) single photon avalanche photodiode (SPAD) illumination is far above the count-rate that causes dead-time of the detectors. This will be referred to as the "dead-time regime."

Through tissues thicker than 1 mm, the vast majority of photons reaching the detector in transillumination (light source and detector on opposite sides of the sample) mode will be diffuse photons, having taken an indirect path through the tissue. The rate of ballistic photons (photons experiencing no scatter or absorption) reaching a detector, $I_b$, can be estimated from the Beer-Lambert Law as follows (note: ballistic fluorescence photons would be approximately 2 orders-of-magnitude lower after taking into account concentration of the fluorophore and the quantum efficiency of the fluorophore):

$$I_b(l) = I_0 e^{-(\mu_a + \mu_s)l}, \quad (1)$$

where l is the diameter of the sample being imaged, μa and μs are the absorption and scattering coefficients of light in the tissue, respectively, and $I_0$ is the rate of photons emitted from the light source: typical values of μa and μs being 0.02 mm$^{-1}$ and 10 mm$^{-1}$, respectively, in the near-infrared regime (700-900 nm).

A comparative rough approximation of the rate of all photons (ballistic+scattered) reaching the detector in diffuse media can be estimated by the diffusion approximation to the radiative transfer equation, which, in its most basic form (infinite homogeneous medium) has the following form:

$$I_{all}(l) = I_0 \frac{NA}{4\pi l} e^{-\sqrt{3\mu_a(\mu_a + (1-g)\mu_s)} \, l}, \quad (2)$$

where g is the anisotropy of the scatter and is generally considered to be approximately 0.9 for biological tissue, and NA is the numerical aperture of the detector (proportional to the angle of light acceptance). Assuming NA=0.05, g=0.9, μa=0.02 mm$^{-1}$, and μs=10 mm$^{-1}$, the proportion of detected photons that are ballistic as a function of sample thickness can be roughly simplified to:

$$\frac{I_b(l)}{I_{all}(l)} = \frac{4\pi l}{NA} e^{-(\mu_a + \mu_s - \sqrt{3\mu_a(\mu_a + (1-g)\mu_s)})l} = 80\pi l e^{-9.77l}. \quad (3)$$

Equation (3) estimates that through 1 mm tissue, as many as 1 in 70 near-infrared photons reaching the detector may be ballistic, suggesting there is a strong potential to significantly improve spatial resolution with time-resolved detection approaches in this regime. However, as tissue thickness increases, the exponential nature of Eq. (3) dominates, and by 4 mm, as few as 1 in $10^{14}$ photons reaching the detector are ballistic. While very rare, it is possible to safely illuminate tissue with as many as $10^{19}$ photons/s at 785 nm based on pulsed laser ANSI safety limits for skin (a conservative limit for tissue samples). As such, based on Eq. (1), it is conceivable that approximately 40 ballistic photons could be reaching a detector every second even at 4 mm tissue thickness. Now in order to separate ballistic from diffuse photons at the detector, one would require a detector with as fine a temporal resolution as possible. To date, the best temporal resolution is provided by time-correlated single photon counting (TCSPC) systems, typically using either photomultiplier tubes (PMTs) or SPADs to amplify the signal from a single photon event. However, conventional use of such systems has aimed to keep photon count-rates low enough to limit dead-time/"pile-up" effects (i.e., limiting the occurrence of more than one photon arriving at the detector within the duration of the dead-time of the system—so that all but the first photon will not be detected).

Figure 4A:
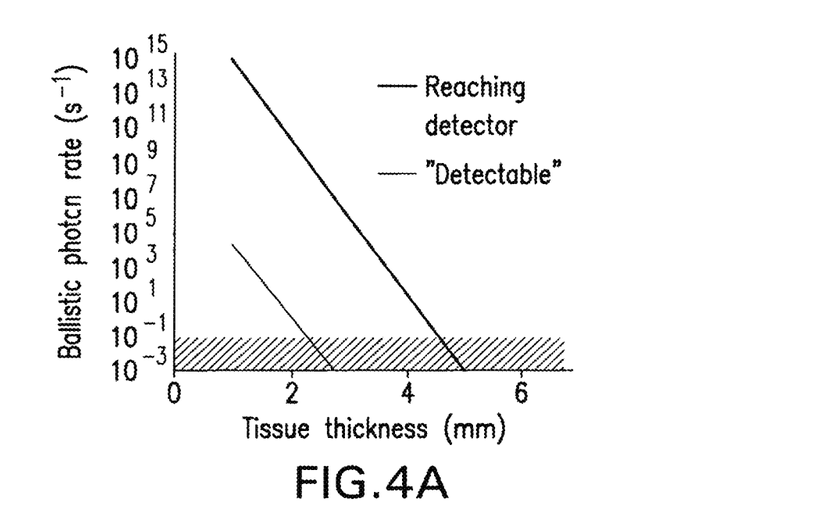
FIG. 4A is a plot according to one example of this invention.

With current pulsed lasers and TCSPC detection systems, the maximum count-rate is approximately $10^6$ photons/s to remain below this dead-time limit, yet at this rate, there would be approximately 3 years between every ballistic photon detection through 4 mm of tissue, far below background levels and approximately 10 orders-of-magnitude below the theoretical rate of ballistic photon detection based on ANSI safety limit thresholds for laser power (~40 ballistic photons per second—FIG. 4A).

Using relatively robust SPAD detectors rather than PMTs for TCSPC—the latter of which is sensitive to overheating damage with high photon incidence rates—can allow for use of higher-powered light sources. And while longer dead-time of these detectors also limits the maximum photon count rate to ~$10^6$ per second, as long as the inverse of the laser repetition rate is longer than the dead-time of the TCSPC system, the earliest arriving photons within each pulse period will be detected preferentially to any later arriving photons. In other words, the use of SPAD-based TCSPC systems in a dead-time regime can provide a means to significantly enhance the number of detected early photons while the later arriving photons will become increasingly masked by the detector's dead-time at photon rate at the detector increases.

Detecting and discriminating truly ballistic photons may not be possible with current temporal resolution limitations in TCSPC; however, significant improvements in spatial resolution have been demonstrated by carrying out image reconstruction only on the photons in the earliest time gate possible. So, while the preceding theoretical handling of the problem focused on ballistic photon statistics for simplicity, the principles can be scaled to the population of photons arriving within the earliest gate of the TCSPC system. Therefore, by exposing TCSPC detection systems to pulsed light sources that will far exceed the detection dead-time limit of the detector, many orders-of-magnitude improvement can be achieved in the probability of detecting photons arriving in the earliest detectable gates. The example described below explored these dead-time improvements in more detail through simulation and phantom experiments, demonstrating that the number of detected early photon remains linear at high laser power, and significant improvements in spatial resolution can be achieved by even marginally enhancing laser power.

Figure 4B:
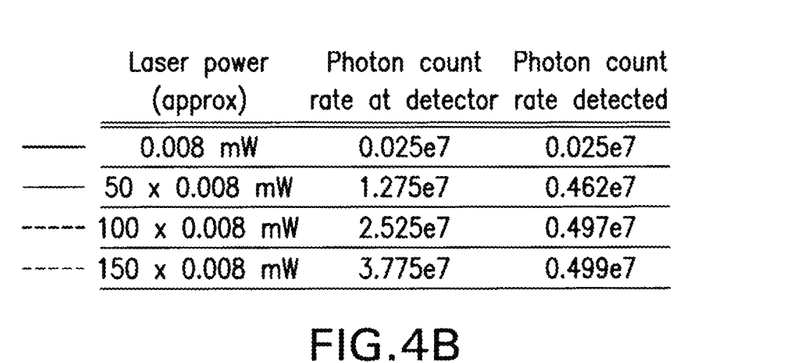
FIG. 4B is a table of photon count at different laser powers.
Figure 4C:
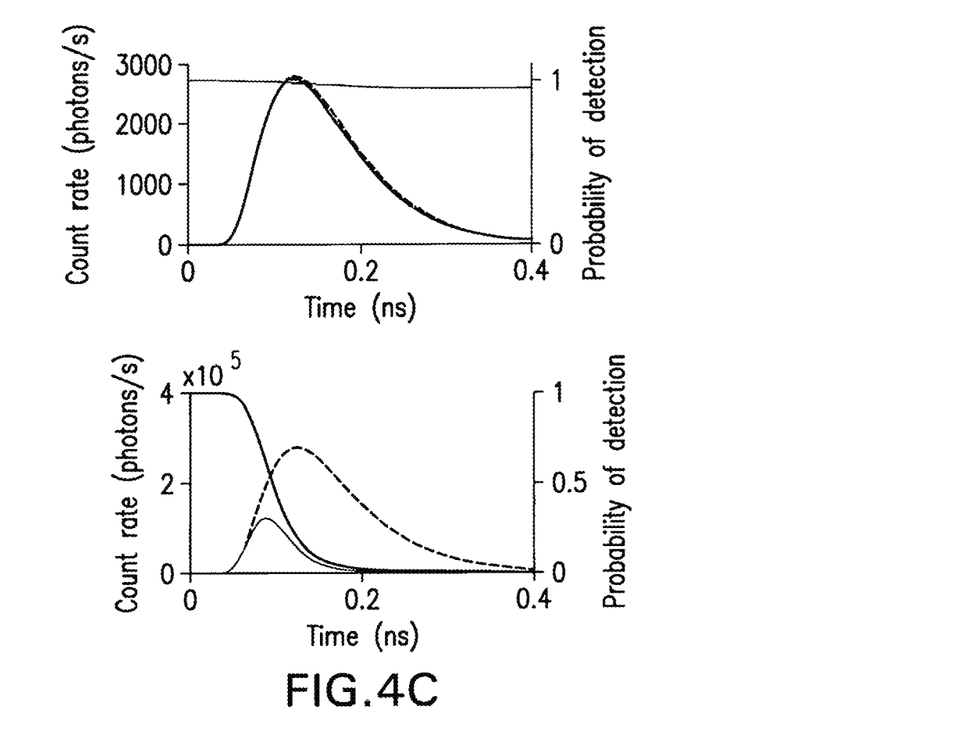
FIG. 4C includes two plots of count rate and probability of detection.
Figure 4D:
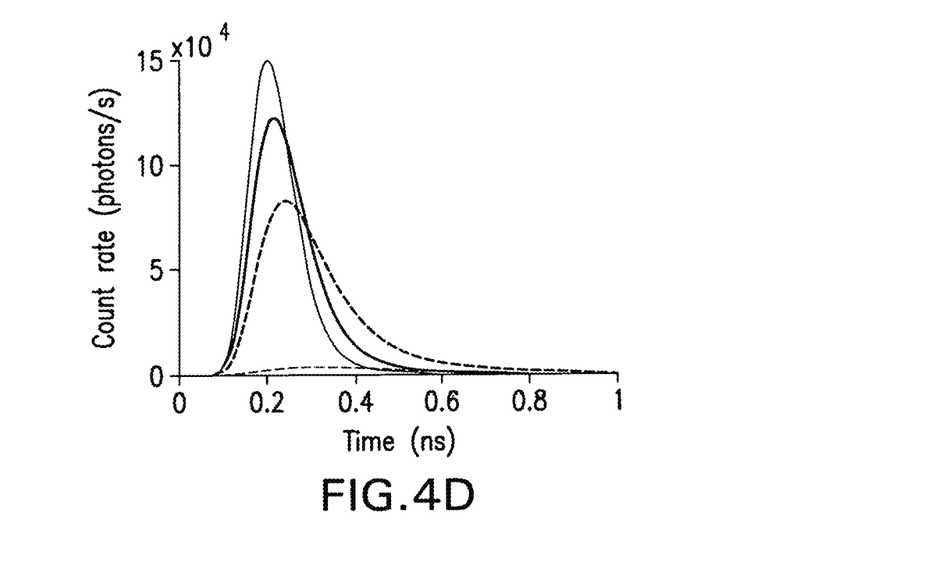
FIG. 4D is a graph of count rate vs. time.

The analytical solution of photon propagation through a 5-mm thick tissue was used to simulate a typical photon tissue-transit-time point-spread-function with reduced scattering coefficient $\mu_s'=10$ mm$^{-1}$ and absorption coefficient $\mu_a=0.02$ mm$^{-1}$. This solution was then scaled to various photon count rates in 4 ps time bins (matching the characteristics of the TCSPC system described below) by normalizing to power levels achievable experimentally with an LDH-PC780 pulsed-diode laser (PicoQuant, Berlin, Germany). The saturation and dead-time effect of the detector were implemented with an assumption that the dead-time was 80 ns (comparable to the detector in the system described below). The table in FIG. 4B demonstrates that with increasing laser power, the rate of photons reaching the detector increased linearly; however, because of the dead-time effect, the maximum rate of photon detection saturated at about $5 \times 10^6$ photons/s assuming a laser pulse repetition rate of 5 MHz. The plots in FIG. 4C demonstrate that the rate of photons detected will underestimate the rate of photons incident on the detector at higher laser powers, with photon count rates in later gates decreasing as governed by dead-time effect principles. FIG. 4D demonstrates that with increasing power, the dead-time effect leads to an apparent shift in photon arrival time detection to earlier gates, thus boosting the probability of early photon detection at the expense of late arriving photon counting. This shift is not a true shift to earlier photons. In fact the shape of the photon arrival time distribution incident on the detector did not change, only the scale increased (dashed curve in FIG. 4C). The probability of detecting photons arriving in the early gates remained unchanged with laser power, while the probability of detecting the later-arriving photons diminished significantly with increased laser power because of the dead-time of the detector.

Figure 5:
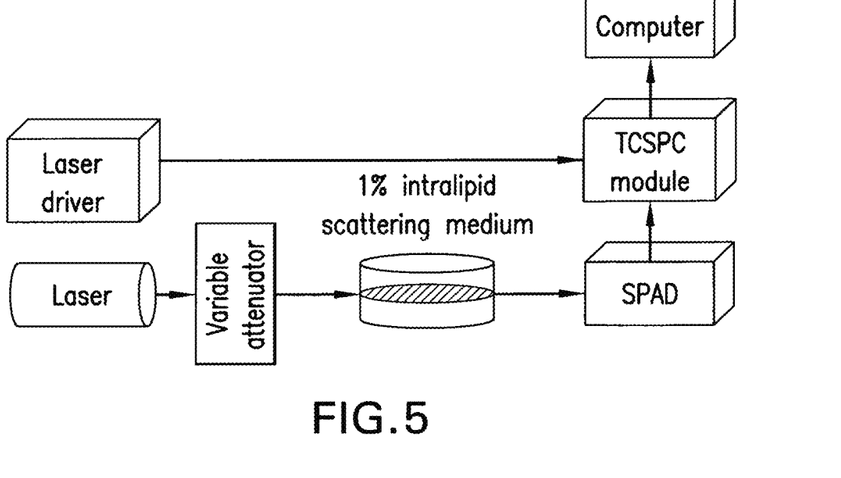
FIG. 5 is a block diagram of a fluorescent imaging system according to one embodiment of this invention.

FIG. 5 illustrates a further experimental setup used to test these theoretical improvements in early photon count rate when in the dead-time regime of TCSPC, and included as a excitation light source a 785±4 nm wavelength pulsed-diode laser (LDH-PC780, PicoQuant) powered by a laser driver (PDL 800-B, PicoQuant) working at a 5 MHz repetition rate and at full power. The pulse width of this laser is approximately 100 ps (note: shorter pulsed lasers are available that could further enhance this dead-time regime methodology; however, this laser is sufficient for demonstrating the effect in principle). A 0-4 OD circular variable attenuator (Thorlabs, Newton, N.J.) was used to control the power of the laser source incident on the scattering medium without changing the shape of the laser pulse. The laser power exiting the variable attenuator was monitored with a power meter (S120C, Thorlabs). A 5-mm diameter cuvette filled with 1% Intralipid® (Sigma-Aldrich, St. Louis, USA) and India ink (Winsor & Newton, London, UK) in water to match the optical properties of the simulations was used as a phantom. The transmitted signal was then detected by a SPAD (PDM, PicoQuant) connected to a TCSPC module (PicoHarp 300, PicoQuant) to obtain temporal information at 4±25 ps temporal resolution over the 200 ns pulse repetition period and with a dead-time of approximately 80 ns. The TCSPC system and laser driver were connected through a TTL port to reference the time of arrival of each photon to the nearest laser pulse. All control of the system was carried out with in-house software developed in MAT-LAB.

Figure 6A:
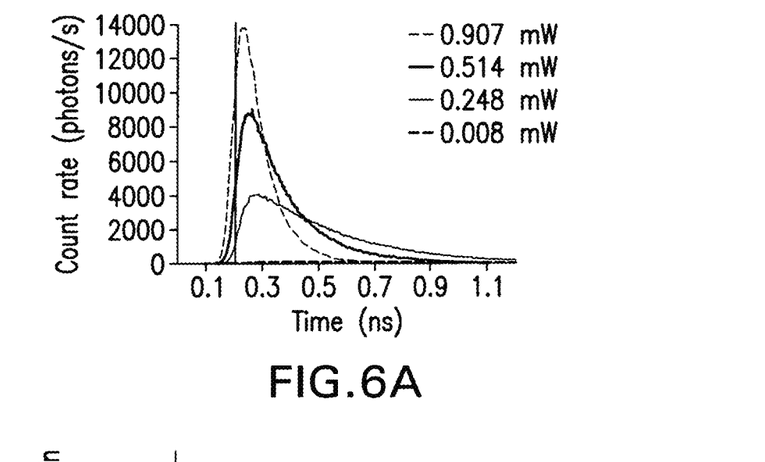
FIG. 6A is a graph summarizing testing results of the system of FIG. 5.

Attenuation of the laser down to a power of 0.008 mW was needed to completely avoid dead-time effects at the detector (FIG. 6A). This occurs with this TCSPC approach when the inverse of the rate of photon detection is less than 1% of the duration of the dead time (~80 ns), capping the photon detection rate at approximately $1.25 \times 10^5$ photons/s. Increasing the laser power above this threshold triggered a warning on the built-in PicoHarp software, to notify the user that dead-time effects may be affecting photon count rates. Since the purpose of this study was to evaluate the effects of this dead-time in aiding detection of rare early photons, the variable attenuator was decreased to increase power over a range from 0.008 mW all the way up to 0.9 mW, which was the maximum power of the laser under the defined settings. This was well below the ANSI safety limit for skin, which is ~2 W for this wavelength and type of light source. With ANSI safety limits being conservative limits for in vivo human studies, it is conceivable that the laser power could be increased by up to 4 or 5 orders of magnitude compared to what was used as a maximum power in the current study, further supporting the enormous potential of detecting early photons in a dead-time regime.

Figure 6B:
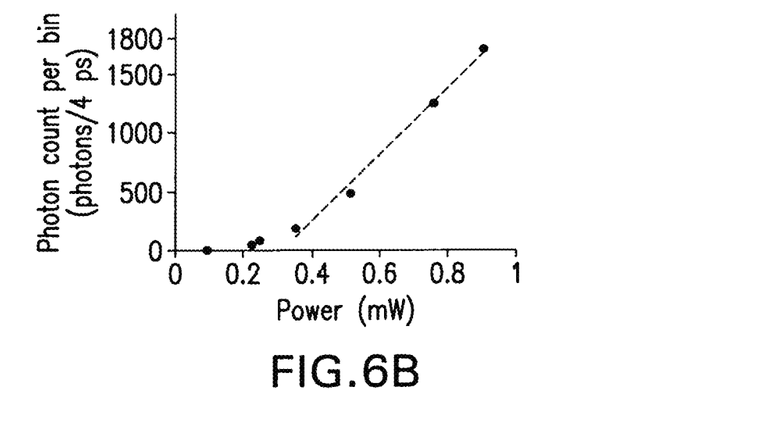
FIG. 6B is a graph summarizing testing results of the system of FIG. 5.

FIG. 6A demonstrates the saturation characteristics observed with dead-time in TCSPC match what was predicted by simulations of dead-time (FIG. 4B); specifically, that early-gate photon count rates increased with increased laser power, while later-gate photon count rates decrease commensurately maintaining the total count rate below the saturation limit for all laser powers yielding photon incidence rates at the detector that exceed 1/dead-time. Moreover, it can be seen that once the laser power was increased enough to achieve photon count rates above the background noise in a given early gate, the signal in that gate remained linear with laser power despite diminished count rates in later gates (FIG. 6B).

Figure 7A:
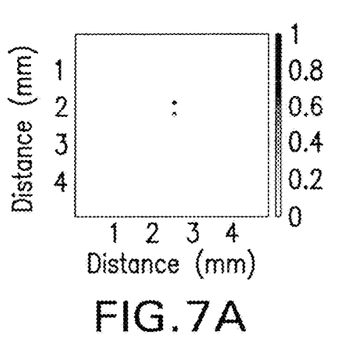
FIG. 7A shows a 5 mm×5 mm sample simulated with fluorescence in two separate 100 μm×100 μm inclusions.
Figure 7B:
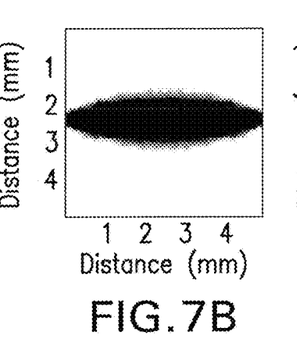
FIG. 7B is an estimated projection profile for dead-time regime early photons.
Figure 7C:
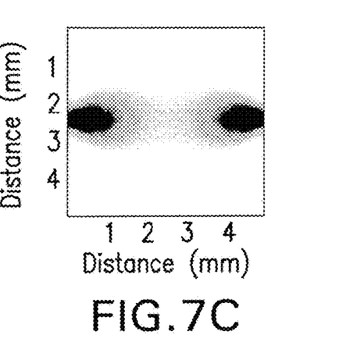
FIG. 7C is an estimated projection profiles for conventional photons.

For further analysis, Monte-Carlo simulation was used to test how much better resolution could be achieved if a certain time window is used for reconstruction. Dead-time regime early gate photons were compared to conventional early gate photons—defined here as gates taken between 1% to 15% of the peak of the measured photon arrival distribution collected at a laser power below the detector dead-time regime. A 5 mm×5 mm sample was simulated with fluorescence in two separate 100 μm×100 μm inclusions (FIG. 7A). Projection profiles were estimated by taking the product of the Monte-Carlo sensitivity photon likelihood path distributions through the sample (for dead-time regime early photons and conventional photons—FIGS. 7B and 7C, respectively), assuming adjacent source-detector positions ranging from 0-5 mm in the vertical direction.

Figure 7D:
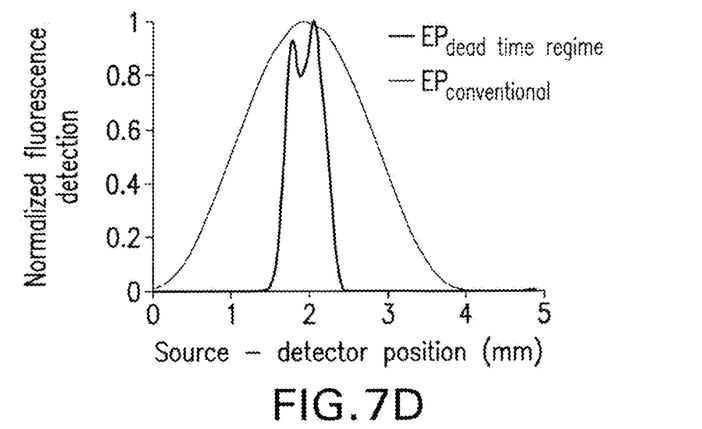
FIG. 7D is a graph comparing dead-time regime early photons to conventional early photons.

FIG. 7D provides a very rough idea of how much better resolution can be obtained with dead-time regime early photons compared to conventional early photons: the FWHM being improved from 1.89 mm in case of conventional early photons compared to 0.56 mm using the earliest detectable gate with the Monte-Carlo. It should be noted that the Monte-Carlo was carried out with $10^8$ photons because of computation time, yet ANSI safety limits would allow for far greater fluence (~$10^{19}$ photons, a rate that is not feasible to simulate with Monte-Carlo), and so the Monte-Carlo data here is likely to suffer from the same issues of inefficient photon detection rates in early gates as with conventional TCSPC detection discussed in the Introduction section. So, even in this very conservative estimate, getting the earliest gate photons in the dead-time regime can provide significant improvements on spatial resolution in diffuse optical tomography over conventional early photons.

Thus, the invention provides a method to enhance detection of low-scattering, early-arriving photons in time-resolved diffuse optical tomography. By running a TCSPC detector in a dead-time regime, detection of early arriving photons can be maintained while only later arriving photons will be affected by dead-time. The simulations suggest that up to at least 10 orders-of-magnitude improvement in early photon detection can be achieved through tissues thicker than a few millimeters. Furthermore, the experiments demonstrate this phenomenon, highlighting the fact that the earliest photons, once detected at rates higher than the background level, are detected in a linear fashion for a wide range of laser powers (and despite the severe nonlinearity of later-arriving photon detection in this regime).

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method for detecting early photons in optical projection tomography, comprising:
   providing a pulsing stimulus light and a detector;
   generating a first pulse of the stimulus light at and through a light scattering object;
   detecting only a first excitation or emission photon that arrives at a detector for the first pulse of the stimulus light, wherein additional photons of the first pulse arrive at the detector during a first dead-time of the detector;
   reactivating the detector after completion of the first pulse through the light scattering object, thereby correlating the timing of the first pulse with the first dead-time of the detector;
   generating a subsequent pulse of the stimulus light through the light scattering object after the first pulse and upon the reactivation of the detector;
   detecting only a next first excitation or emission photon that arrives at a detector for the subsequent pulse of the stimulus light, wherein additional photons of the subsequent pulse arrive at the detector during a subsequent dead-time of the detector; and
   reactivating the detector after completion of the subsequent pulse through the light scattering object, thereby correlating the timing of the subsequent pulse with the subsequent dead-time of the detector.

2. The method of claim 1, wherein the pulsing stimulus light provides a detector photon capture rate of greater than 20%.

3. The method of claim 2, wherein the pulsing stimulus light provides a detector photon capture rate of at least 75%.

4. The method of claim 1, further comprising pulsing the stimulus light at a repetition frequency that is less than the inverse of a dead-time of the detector.

5. The method of claim 1, wherein the detector is a single photon counting photodetector.

6. The method of claim 1, further comprising time-stamping each detected photon.

7. The method of claim 1, further comprising providing a telecentric scanning lens adapted to scan a surface of the tissue.

8. The method of claim 7, wherein the scanning lens is positioned opposite an excitation spot to collect light in a parallel geometry.

9. The method of claim 1, further comprising administering a fluorophore contrast agent to the light scattering object, and forming a digital image of the light scattering object from a plurality of detected first excitations.

10. The method of claim 1, wherein the detector comprises a multichannel photodetector adapted to capture data with the light scattering object illuminated at each of a plurality of discrete points in succession, and further comprising machine readable code including instructions for reconstructing a three dimensional model of a fluorophore distribution in the light scattering object from the data.

11. The method of claim 1, further comprising time-stamping detected photon events using time-correlated photon counting.

\* \* \* \* \*